United States Patent
Aleo et al.

(10) Patent No.: US 8,957,110 B2
(45) Date of Patent: Feb. 17, 2015

(54) OPHTHALMIC COMPOSITIONS BASED ON POLYUNSATURATED OMEGA-3 AND OMEGA-6 FATTY ACIDS

(75) Inventors: Danilo Aleo, Catania (IT); Stefano Barabino, Genoa (IT); Sergio Mangiafico, Catania (IT); Maurizio Rolando, Genoa (IT); Maria Grazia Antonietta Saita, Catania (IT)

(73) Assignee: TRB Chemedica International S.A., Geneva (CH)

( * ) Notice: Subject to any disclaimer, the term of this patent is extended or adjusted under 35 U.S.C. 154(b) by 157 days.

(21) Appl. No.: 13/256,994

(22) PCT Filed: Mar. 18, 2010

(86) PCT No.: PCT/IT2010/000119
§ 371 (c)(1),
(2), (4) Date: Sep. 16, 2011

(87) PCT Pub. No.: WO2010/106571
PCT Pub. Date: Sep. 23, 2010

(65) Prior Publication Data
US 2012/0010280 A1    Jan. 12, 2012

(30) Foreign Application Priority Data
Mar. 19, 2009  (IT) .............................. RM2009A0119

(51) Int. Cl.
| *A01N 43/16* | (2006.01) |
| *A61K 31/355* | (2006.01) |
| *A01N 37/00* | (2006.01) |
| *A61K 31/20* | (2006.01) |
| *A61K 9/00* | (2006.01) |
| *A61K 9/06* | (2006.01) |
| *A61K 31/201* | (2006.01) |
| *A61K 31/202* | (2006.01) |
| *A61K 47/32* | (2006.01) |

(52) U.S. Cl.
CPC ................. *A61K 9/0048* (2013.01); *A61K 9/06* (2013.01); *A61K 31/20* (2013.01); *A61K 31/201* (2013.01); *A61K 31/202* (2013.01); *A61K 47/32* (2013.01)
USPC ............................ 514/458; 514/558; 514/560

(58) Field of Classification Search
USPC .......................................... 514/458, 558, 560
See application file for complete search history.

(56) References Cited

U.S. PATENT DOCUMENTS

| 5,458,873 | A | * | 10/1995 | Kawashima et al. | ...... 424/78.04 |
| 6,201,022 | B1 | | 3/2001 | Mease et al. | |
| 2004/0208939 | A1 | * | 10/2004 | Sears et al. | ..................... 424/523 |
| 2006/0009522 | A1 | * | 1/2006 | Dana et al. | ..................... 514/560 |
| 2007/0207116 | A1 | * | 9/2007 | Brown | ......................... 424/78.3 |

FOREIGN PATENT DOCUMENTS

| WO | WO 00/23069 | 4/2000 |
| WO | WO 02/13838 | 2/2002 |
| WO | WO 2004/004599 | 1/2004 |
| WO | WO 2006/004582 | 1/2006 |
| WO | WO 2006/007510 | 1/2006 |
| WO | WO 2007/066232 | 6/2007 |
| WO | WO 2007/109523 | 9/2007 |

OTHER PUBLICATIONS

Aragona, P. et al. "Systemic Omega-6 Essential Fatty Acid Treatment and $PGE_1$ Tear Content in Sjögren's Syndrome Patients" *Invest. Opthalmol. Vis. Sci.*, Dec. 2005, pp. 4474-4479, vol. 46, No. 12.
Barbino, S. et al. "Systemic Linoleic and γ-Linolenic Acid Therapy in Dry Eye Syndrome With an Inflammatory Component" *Cornea*, 2003, pp. 97-101, vol. 22, No. 2.
Creuzot, C. et al. "Amelioration de la symptomatologie chez des patients atteints de secheresse oculaire et traites oralement par des acides gras polyinsatures" *J. Fr. Opthalmol.*, 2006, pp. 868-873, vol. 29, No. 8.
Rashid, S. et al. "Topical Omega-3 and Omega-6 Fatty Acids for Treatment of Dry Eye" *Arch Opthalmol.*, 2008, pp. 219-225, vol. 126, No. 2.
Vandamme, Th. F. "Microemulsions as ocular drug delivery systems: recent developments and future challenges" *Progress in Retinal Eye Research*, 2002, pp. 15-34, vol. 21.
Verbey, N. L. J. et al. "Modulation of immunogenic keratitis in rabbits by topical administration of poly-unsaturated fatty acids" *Current Eye Research*, 1998, pp. 549-556, vol. 7, No. 6.

\* cited by examiner

*Primary Examiner* — Kara R McMillian
(74) *Attorney, Agent, or Firm* — Saliwanchik, Lloyd & Eisenschenk

(57) ABSTRACT

The invention concerns topical compositions for the prevention and treatment of ocular pathologies, in particular inflammatory keratites and conjunctivites and dry eye syndrome, containing as active ingredients polyunsaturated fatty acids of the types omega-3 and omega-6, and specifically EPA (eicosapentaenoic acid), DHA (docosahexaenoic acid) and GLA (γ-linolenic acid), mixed with vitamin E acetate and formulated in a stable composition in hydrogel, i.e. in dispersed form in an aqueous vehicle containing one or more gelling polymers. The proposed compositions are particularly indicated for use as artificial tears.

23 Claims, 2 Drawing Sheets

OPHTHALMIC COMPOSITIONS BASED ON POLYUNSATURATED OMEGA-3 AND OMEGA-6 FATTY ACIDS

CROSS-REFERENCE TO RELATED APPLICATION

This application is the U.S. national stage application of International Patent Application No. PCT/IT2010/000119, filed Mar. 18, 2010.

The present invention relates to ophthalmic compositions based on polyunsaturated omega-3 and omega-6 fatty acids. More specifically, the invention concerns topical preparations for the prevention and treatment of ocular pathologies, in particular inflammatory keratitis and conjunctivitis and dry eye syndrome, containing as active ingredients polyunsaturated fatty acids of the types omega-3 and omega-6, formulated in a stable composition in hydrogel. The proposed compositions are particularly indicated for use as artificial tears.

As it is known, the preocular tear film is a complex liquid structure which coats the exposed surface of the eyeball as well as the bulbar and palpebral conjunctiva. Such structure results from the cooperation of a solid layer, formed by the complex of corneal epithelium and glycocalyx (i.e., the glycoproteins coating of the epithelial cells, consisting of their secretions), with a liquid layer, which is more properly the lacrimal film. The solid layer serves to allow the adhesion of the liquid part of the lacrimal film on the ocular surface, while the liquid layer is in turn formed by three overlapping layers: a mucous layer, an aqueous layer and a lipid layer.

The internal mucous layer of the tear film consists of a mixture of viscoelastic hydrated glycoproteins (mucin), which adhere to the said solid layer and form a hydrophilic surface. The aqueous layer is the intermediate portion of the tear film, which spreads over said hydrophilic surface and is made essentially of water, organic and inorganic salts, sugars, proteins, enzymes and other biopolymers of a complex structure (such as the mucins themselves). The substances in solution in this layer have structural, osmotic, buffering and nourishing functions, and result in the lacrimal film defense for the tissues of the ocular surface. The thin external lipid layer is formed by waxes, fatty acids and cholesterol esters, and serves to stabilize the tear film, by controlling the water loss due to evaporation.

The three-layered structure described makes up a complex physiological system, the main functions of which are to protect the eye surface, to maintain the hydration, lubrication and cleanliness of the corneal surface and to cooperate in producing a proper vision. A perfect balance and a continuous turnover of the lacrimal film are necessary conditions for it to carry out its functions. In particular, a constant but not excessive water evaporation from the tear fluid must take place, so as to keep the osmolarity thereof to the physiological level, and the tear film must be continuously redistributed on the corneal surface as a result of blinking.

As a consequence of abnormalities or unbalances of one or more of the layers described above the condition known as dry eye syndrome or dry eyes (keratoconjunctivitis sicca) may occur, which is a chronic disorder mainly affecting elderly women. Dry eye is a multifactorial pathology characterized by changes in the qualitative and quantitative composition of tear film, which results in foreign body sensation, symptoms of irritation (discomfort), vision disturbances and instability of the lacrimal film, with potential impairment of the ocular surface, and is accompanied by tear film iperosmolarity. Actually, in patients suffering from this pathology an increased evaporation and a reduced turn-over of the tear fluid occurs, with a resulting increase of the film osmolarity, which reaches levels as high as 330-340 mOsm/l, the normal baseline value being about 300 mOsm/l. It is also known that the dry eye syndrome tends to be accompanied by inflammatory phenomena, which extend from the ocular surface to the lacrimal gland and to the meibomian glands.

Dry eye syndrome has generally a severe impact on the quality of life of patients suffering from it and remarkable social costs, owing to the fact that its symptoms are chronic, that the visual ability both at work and in ordinary activities (reading, watching TV, driving) is reduced, and that it is necessary to have frequent recourse to examination by an ophthalmologist and to medical therapies. Considering the progressive increase of the average age of the human population, such disease is going to have an ever increasing importance in the future.

The therapies for dry eye syndrome are mainly focused on restoring the tear film, e.g. by employing slow release ocular inserts to be inserted in the conjunctival sac and, above all, with liquid ophthalmic preparations, generally known as "artificial tears", to be instilled in drops in order to replace or integrate the natural tears production. In the simplest case such preparations have a moistening action only, as they consist of physiological saline solutions, neutral and isotonic with the tear fluid, based on sodium chloride only or on balanced mixtures of various electrolytes. In other cases, in order to overcome the drawback of the reduced retention in the conjunctival sac and to lubricate the tissues and more effectively prevent the formation of dry areas in the corneal epithelium, the tear substitute formulations are enriched with high molecular weight components having functions of viscosifying agents. Such components are normally water-soluble polymers of a synthetic, semisynthetic or natural origin, many of which, such as hyaluronic acid and cellulose derivatives, have reached a widespread diffusion for the concerned use.

It is to be noted that in case of alterations or insufficiency of the external lipid layer of the lacrimal film, the continuous exposure of the film to the external environment may result in evaporation of the aqueous component, exposure of the ocular surface to infective agents and consequent inflammation of the same ocular surface. These mechanisms underlie the clinical symptoms and signs of dry syndrome, but can also occur in normal subjects exposed to low humidity and low air flow environments.

Owing to the inflammatory component which is generally present in dry eye syndrome, compounds such as polyunsaturated fatty acids, in particular of the type omega-3 and omega-6, are quite interesting for a possible inclusion thereof in tear substitute preparations. As it is known, polyunsaturated fatty acids or PUFA are carboxylic compounds with aliphatic chain having two or more double bonds in the chain, which are characterized by the position of the first double bond starting from the terminal carbon atom of the chain (ω position). Among the polyunsaturated fatty acids, omega-3 (or PUFA n-3) and omega-6 (or PUFA n-6) represent a group of essential fatty acids, indispensable for a proper functioning of the body. Examples of omega-3 fatty acids include α-linolenic acid (C18:3, n-3; ALA), eicosapentaenoic acid (C20:5 n-3; EPA) and docosahexaenoic acid (C22:6, n-3; DHA); examples of omega-6 fatty acids include linoleic acid (C18:2, n-6; LA) and γ-linolenic acid (C18:3, n-6; GLA).

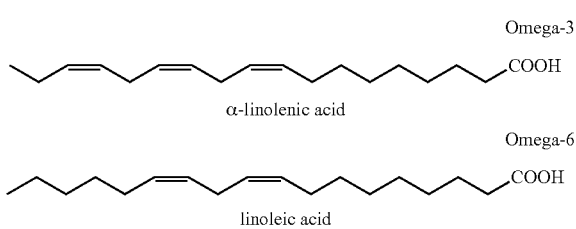

α-linolenic acid (Omega-3)

linoleic acid (Omega-6)

It is reported in the literature (N. L. J. Verbey, N. J. van Haeringen, P. T. V. M. de Jong. *Current Eye Research*, 1988, 7(6) 549-556) that the topical treatment of the ocular surface with unsaturated fatty acids of the type omega 3 and omega 6 is effective in inhibiting various processes such as leucocytes infiltration, neovascularization and corneal edema, all these being expressions of the inflammatory phenomenon. The fatty acids that have shown to be the most active ones are eicosapentaenoic acid (EPA, omega-3) and γ-linolenic acid (GLA, omega-6). The mechanism of action of these acids is connected to the mechanism of action of arachidonic acid in the inflammatory cascade: actually, they are in competition with arachidonic acid in inhibiting the formation of prostaglandins E1 (PGE1) and proinflammatory leukotrienes.

Nutraceutical supplements based on polyunsaturated fatty acids, rich in omega-3 fatty acids, taken from fish oils (in particular, salmon and herring oils) and in omega-6 fatty acids, mostly of a vegetal origin (blackcurrant, borage) are widely employed in view of their beneficial activity on the cardiovascular, immune and nervous system and also, specifically, for use as supplements in the treatment of dry eye. As a matter of fact, recent works have shown that both EPA and GLA exert a significant therapeutic activity in dry eye syndrome (Aragona, P., et. al., Systemic omega-6 essential fatty acid treatment and PGE1 tear content in Sjogren's syndrome patients. *Invest. Ophthalmol. Vis. Sci.*, 2005. 46(12): 4474-9; Barabino, S., et. al., Systemic linoleic and gamma-linolenic acid therapy in dry eye syndrome with an inflammatory component. *Cornea*, 2003. 22(2): 97-101; Creuzot-Gracher, C., et. al., Improvement of dry eye symptoms with polyunsaturated fatty acids. *J. Fr. Ophthalmol.*, 2006 29(8): 868-73). It is to be noted that the concerned products are, also in case of ophthalmic indications, products for oral administration.

Although about two decades have passed since the demonstration that topical use of omega-3 and omega-6 fatty acids results in beneficial effects on affections of the ocular surface, to date no eye-drops containing the said fatty acids are available on the market. It is clear that such availability would bring about remarkable advantages in the treatment of dry eye syndrome, firstly due to the better tolerability of a topical ophthalmic product in comparison with a product for oral administration, the use of which affects the gastrointestinal tract. Such lack is to be ascribed to the difficulty of formulating fatty acids of the kind of EPA and GLA, above all in view of the poor water solubility and poor chemical stability of these active ingredients.

Therefore, polyunsaturated fatty acids, being highly lipophilic and poorly water soluble molecules, presently represent a challenge for researchers seeking for new aqueous ophthalmic preparations for topical administration.

Lipid emulsions, used since long time for parenteral applications, have been studied in order to formulate several lipophilic active ingredients and enhance their ocular bioavailability (T. F. Vandamme, Microemulsions as ocular drug delivery systems: recent developments and future challenges, *Prog. Retin. Eye Res.* 21 (2002) 15-34; S. Tamilvanan, R. N. et. al., Emulsion-based delivery systems for enhanced drug absorption, *Pharm. Tech.* 131 (2002) 156-161). As it is known, emulsions are disperse systems formed by two immiscible liquid phases, prepared through mechanical stirring. Given the difference of attractive interaction between the different molecules of the two liquid phases, an interfacial tension is generated in each point where the two liquids are in contact, and due to said tension the two liquid phases tend to separate from each other, to minimize the contact surface. The interface tension may be significantly reduced by adding amphiphilic molecules or surface active agents soluble at least in one of the two phases making out the emulsion. Therefore, adding a suitable surface active agent can avoid the separation of the aqueous phase from the oil phase, or at least it can slow down its evolution.

Lipid emulsions for use as medicinal preparations, in particular, pharmaceutical compositions consisting of emulsions of the type oil-in-water for use as carrier of lipophilic active ingredients are disclosed in the document EP 0391369 (Yissum Research Development Company of the Hebrew University of Jerusalem, inventors B. Simon and L. Menashe). Such compositions comprise an oily vehicle consisting of medium chain triglycerides (MCT), optionally combined with a vegetal oil, such as, e.g., soybean oil, together with phospholipids (e.g., lecitins, or soy phospholipids) and surface active agents, in particular nonionic surfactants (such as, e.g., polysorbate 80 or Tween 80) and ionic surfactants (in particular, cholic and desoxycholic acids).

The compositions described in the cited document are reported as giving rise to emulsions with high stability, and are proposed for oral, parenteral and also topical ophthalmic administration of lipophilic active ingredients. Among these the examples describe amphotericin B and miconazole base.

In the frame of the research carried out by the Applicant aimed at providing an ophthalmic product in eye-drops based on polyunsaturated fatty acids, the possibility of preparing a composition containing eicoesapentaenoic (EPA) and γ-linolenic (GLA) acids as active ingredients by using the lipid emulsion model of patent EP 0391369 has been explored. The results of such experimentation, synthetically reported further on (see Comparative Example 1) have shown that the emulsions based on omega-3 and omega-6 fatty acids obtained in this way are quite unstable from the physical point of view, since they tend to evolve towards the phase separation, and above all they are unstable from the chemical point of view, since the title of the two active ingredients is remarkably reduced already after the first month of storage in refrigerated conditions (at a temperature of 4° C.), very likely due to oxidation.

Since the main degradation products responsible for the reduction of EPA and GLA concentration in the experimentation carried out were oxidation products, an attempt is also been made to prepare such emulsion under nitrogen blanket, by sparging nitrogen in the emulsification step, and in the presence of antioxidants (such as vitamin E and Trolox, a water-soluble derivative of the latter). Also in this way, however, the emulsion turned out to be chemically unstable and after one month of storage at room temperature the concentration of EPA and GLA had decreased to unacceptable values (see Comparative Example 2). The experimental results obtained evidence the impossibility of storing the eye-drop product concerned for the time periods required to a pharmaceutical product, both at room temperature and under refrigerated conditions.

More recently, the international patent application publ. No. WO 2006/007510 (R. Dana et al., assigned to Schepens Eye Research and Johnson & Johnson Vision Care, Inc.) disclosed topical ophthalmic compositions based on omega-6 and omega-3 fatty acids as active ingredients, starting from the acknowledged anti-inflammatory activity of such agents and from the consideration that an oral administration of the same, which is in use since long time, may be scarcely tolerated or undesired.

In the preparations exemplified in such document omega-3 and omega-6 are directly emulsified with suitable surfactants, such as e.g. polyethoxylated sorbitan fatty acids esters (namely, polisorbates such as "Tween") and polyethoxylated methyl glucosides (such as "Glucam"). Specifically, in the preparation process disclosed a first surfactant is added to a buffered saline solution and the mixture is kept under stirring, at room temperature, for a time sufficient to obtain a clear solution; then a second surfactant is added and subsequently, after a further period of mixing, the fatty acid (or fatty acids, in the event these are more than one) is/are added very slowly. Finally, a drop of vitamin E is added (with antioxidant function) and the emulsion is kept under stirring for some hours more.

The same research group has recently published (S. Rashid et al., Topical Omega-3 and Omega-6 Fatty Acids for Treatment of Dry Eye, *Arch. Ophthalmol.* 126(2) (2008) 219-225) the results of a clinical trial on the effectiveness of the topical administration of preparations of α-linolenic acid (ALA) and linoleic acid (LA) in the treatment of dry eye, where the tested preparations had been obtained by emulsifying the active ingredients with Tween-80 (2.6%) and Glucam E-20 (2.6%) in aqueous solution, as reported in the cited patent document.

Nothing is reported, however, either in the patent publication WO 2006/007510 or in the related scientific article, as concerns the physical stability of the polyunsaturated fatty acids in such ophthalmic preparation, nor as concerns their chemical stability. It has however been ascertained through an experimentation carried out by the present Applicant, reported further on (see Comparative Example 3), that preparations based on EPA, DHA and GLA obtained in emulsion according to the teachings of such document suffer from oxidation problems similar to those observed with the preparations in phospholipidic emulsion previously described.

The difficult physical stability of the emulsions, obtained only by using remarkable amounts of surface active agents (which are assumed to be toxic for the corneal surface) and, above all, the chemical instability of the polyunsaturated acids of interest call for new pharmaceutical systems alternative to those described above with reference to the prior art.

In the frame of the studies carried out in connection with the present invention it has been considered that aqueous hydrogels formed by hydrophilic polymers are able to trap and keep in suspension strongly hydrophobic active ingredients without needing to have recourse to the emulsions technology. It has been found, therefore, according to the present invention, that it is possible to incorporate some specific polyunsaturated fatty acids of the types omega-3 and omega-6, or suitable derivatives thereof, in solution with an antioxidant of the vitamin E family (i.e. tocopherols and their pharmaceutically acceptable esters), in the structure if the tridimensional network of a hydrogel, thus obtaining preparations which are stable to storage, both in refrigerated conditions and at room temperature, easily administerable in the form of eye-drops and quite well tolerated in the eye.

Several medicaments are presently on the market which are formulated as gels for topical ophthalmic administration, such as, e.g. Timoptol XE (Merck Sharp & Dohme), based on timolol maleate, having a gelling system containing gellan gum, and Nyogel (Novartis), also containing timolol maleate as the active ingredient, carried in a polyvinyl alcohol (PVA) gel and Carbomer 974 (belonging to the family of carboxyvinyl polymers also known as "CARBOPOLS"). However, to date these systems have been employed with the only purpose of ameliorating the bioavailability of hydrophilic active ingredients such as, actually, timolol maleate, so as to obtain sustained release delivery systems through the use of which the number of daily administrations of the drug could be reduced, and not with the purpose of improving the stability of lipophilic active ingredients.

The ophthalmic preparation proposed according to the invention consists, in synthesis, of a micrometric dispersion of oils that are sources of omega-3 and omega-6 fatty acids with vitamin E, preferably in the acetate form, in an aqueous means, the said dispersion being obtained by employing suitable gelling polymers. As it will be more evident with reference to the experimental section presented further on, the hydrogels containing tocopheryl acetate together with polyunsaturated fatty acids as the carried active ingredients turned out to be surprisingly stable on storage, and maintained their content of active ingredient practically unaltered for long periods of time.

It is to be noted that the ophthalmic products in gel according to the invention, besides acting as carriers of anti-inflammatory products, are useful to protect and integrate the thin lipid layer of the tear film, as the active ingredients at issue are made out of lipid molecules. The integration of the lipid component allows to reduce an excessive evaporation of the lacrimal fluid, while restoring the protective function of the external lipid film. The latter, as it is known, in cases of inflammatory events and in particular in inflammations of the Meibomian glands appears to be altered and unsuitable to counteract the increased evaporation of the aqueous layer (this being a quite frequent event in patients suffering from keratoconjunctivitis sicca).

Therefore, the present invention specifically concerns a topical ophthalmic composition containing, as active ingredients, one or more omega-3 polyunsaturated fatty acids and one or more omega-6 polyunsaturated fatty acids, the said fatty acids having an aliphatic chain of from 16 to 24 carbon atoms, or pharmaceutically acceptable derivatives thereof selected from their esters with $C_1$-$C_6$ alkyl groups, their triglycerides and their phospholipids, in solution with vitamin E or a pharmaceutically acceptable ester thereof, the said solution being in dispersed form in a hydrogel based on an aqueous vehicle containing one or more gelling polymers.

In the preparations according to the invention, vitamin E may be represented by any one of the eight components of the family, α-, β-, γ-, δ-tocopherol and α-, β-, γ-, δ-tocotrienol, but α-tocopherol is preferred in view of its larger diffusion. Among the corresponding esters, besides succinate or long chain acid esters, the most convenient and widespread product is acetate. The preferred antioxidant for the preparations of the present invention is α-tocopheryl acetate, which, compared to the corresponding α-tocopherol, is more tolerable for a topical ophthalmic administration.

It is important to note that in the formulation proposed herein α-tocopheryl acetate may be employed in great amounts, differently from what it happens in a classical emulsion formulation, where the emulsifiable amounts are quite low. On the ocular surface α-tocopheryl acetate gives by hydrolysis α-tocopherol (vitamin E) which, besides having a strong antioxidant effect, is a COX-2 inhibitor, responsible for the synthesis of prostaglandin E2 (PGE2). The latter, as it is known, plays an important role in inflammation. Vitamin E is, in addition, capable of inhibiting the formation of interleukin-1, which is responsible for the tear secretion reduction.

According to some specific embodiments of the invention, each of the said omega-3 and omega-6 fatty acids has an aliphatic chain with two or more double bonds and a length of from 18 to 22 carbon atoms, as well as a carboxy) terminal of the formula COOR, wherein R may be hydrogen or a linear of branched $C_1$-$C_6$ alkyl group. In addition, the carbon atoms of the R group may be chiral.

The terminal group R is selected, preferably, from ethyl, propyl and isobuthyl, and the resulting compounds are, therefore, the ethyl, propyl or isobuthyl esters of the corresponding polyunsaturated fatty acid.

Specifically, a preferred composition according to the invention contains, as omega-3 active ingredients in the α-tocopheryl acetate solution in its turn dispersed in the hydrogel vehicle, eicosapentaenoic acid (EPA), docosahexaenoic acid (DHA) or mixtures thereof, or one or both the respective $C_1$-$C_6$ alkyl esters, or one or both the respective triglycerides or one or more the respective phospholipids.

Similarly, according to another preferred embodiment of the invention, the proposed composition contains, as omega-6 active ingredient in the α-tocopheryl acetate solution in its turn dispersed in the hydrogel vehicle, γ-linolenic acid (GLA) or a $C_1$-$C_6$ alkyl ester thereof, or the respective triglyceride or a phospholipid thereof.

Preferably, the ophthalmic composition according to the invention contains as active ingredients EPA, DHA and GLA, or their ethyl esters, their triglycerides or their phospholipids.

The sources of polyunsaturated fatty acids enriched in acids of the omega-6 family (such as GLA) may be selected from the group of vegetal oils, including:

Linseed oil, borage oil, wheat germ oil, hempseed oil, olive oil, peanuts oil, blackcurrant oil and soybean oil.

The sources of polyunsaturated fatty acids enriched in acids of the omega-3 family (such as EPA and DHA) may be easily found in high concentrations in fish oils, and may be selected from:

Salmon oil, mackerel oil, oily fish (e.g., anchovies and sardines) oil, krill oil and mixtures thereof.

In particular, krill oil is an oil extracted from tiny crustaceans (krill) which are part of the zooplankton, in particular one species of krill that lives in remarkable concentrations in polar and cold waters. Such oil is particularly rich of omega-3 fatty acids similar to those of fish oil, and of phospholipid-conjugated omega-3 fatty acids, mainly phosphatidylcholine (which is often referred to in the field of dietary supplements, for this reason, as marine lecithin).

Fatty acids of the omega-3 family are normally contained in such oils in percentages variable from 40 to 50%, and are also present in the vegetal oils mentioned above as sources of omega-6 fatty acids.

In particular, the pharmaceutical use of EPA, GLA and DHA may be carried into practice by means of starting materials with a high degree of purity. This requires separation of the said fatty acids from the fatty acids mixtures of fish oils and/or vegetable oils, to reach a purity of 90% and 70% respectively for EPA and GLA. The processes presently known for that purpose include: extraction, molecular distillation and low temperature crystallization.

Therefore, according to some preferred embodiments of the invention, the polyunsaturated omega-3 and omega-6 fatty acids contained as the active ingredients in the preparation are contained in one or more vegetal oils and/or in one or more fish oils mixed in turn with the tocopherol antioxidant in which they are soluble, and the mixture is dispersed in micrometric droplets in the aqueous gel. Preferably, the vegetal oils are selected from linseed oil, borage oil, wheat germ oil, hempseed oil, olive oil, peanuts oil, blackcurrant oil and soybean oil, and the fish oils are selected from salmon oil, mackerel oil, oily fish oil, krill oil and mixtures thereof.

In the composition according to the invention the ratio of omega-3 to omega-6 may range from 20:1 to 1:20, preferably from 1:10 to 10:1. In particularly preferred compositions the weight ratio of (EPA+DHA) to GLA is comprised between 4:1 and 1:4.

As it will be more evident with reference to the following examples, the amount of vitamin E in the oily mixture of omega-3 and omega-6 is preferably not less than 50% by weight, and in some preferred formulations it is comprised between 50% and 75% by weight. The preparation based on optionally esterified vitamin E containing the polyunsaturated fatty acids may be readily distributed in a hydrogel, where it is stably dispersed without any phase separation and, above all, it continues to keep its integrity as a solution and therefore its stability, also chemical. The dispersion of the solution of vitamin E acetate containing polyunsaturated omega 3 and 6 fatty acids may take place, surprisingly, up to percentages of 25% by weight of the said oily solution with respect to the total preparation. According to what proposed with the present invention, α-tocopheryl acetate is previously mixed with the source of omega-3 and mega-6 in a ratio with them which may range from 4:1 to 1:4, preferably from 3:1 to 1:3, and more preferably from 3:1 to 1:1, and in a final concentration in the preparation which may vary from 0.1% to 20%.

The gelling polymers proposed for the hydrogel preparation according to the invention are, preferably, products already employed in the common clinical practice, in particular as components of tear substitutes. Such components are chosen from the products which do not alter the qualitative composition of the tear film, and, in addition, may have an auxiliary action besides the anti-inflammatory action of the polyunsaturated fatty acids.

Among the gelling polymers that may be employed, also in combination with each other, in the ophthalmic composition of the invention there are to be considered, by preference, carboxyvinyl polymers (known as CARBOPOL or Carbomer), hyaluronic acid and the salts thereof with alkali and alkali-earth metals, cellulose esters and ethers (such as hydroxypropylcellulose, hydroxypropylmethyl-cellulose, etc.), xanthan gum, alginic acid and alginates and gellans. Other gelling polymers employed in the formulation of artificial tears suitable to avoid an excessive evaporation from the aqueous tear layer could also be used, however, for the purposes of the invention.

In the preferred embodiments of the ophthalmic composition according to the invention the said gelling polymer belongs to the family of variously cross-linked carboxyvinyl polymers known as CARBOPOL (or carbomer). In particular, in the compositions based on EPA and GLA or EPA, DHA and GLA as the main active ingredients, some examples of which are presented herein, the use of CARBOPOL 980 or of CARBOPOL 974 have been particularly advantageous, in concentrations ranging from 0.01% to 5% by weight on the total of the composition, preferably around 0.2% by weight.

The composition according to the invention may also comprise one or more polymeric emulsifying agents selected, for instance, from acrylic acid polymers (such as the product known with the commercial name "PEMULEN", a high molecular weight copolymer of acrylic acid and long chain alkyl methacrylate cross-linked with allyl esters of pentaerythritol) and poloxamers (block copolymers polyoxyethylene-polyoxypropylene, such as the products known as "Pluronic"). In the preferred compositions according to the invention based on EPA and GLA or EPA, DHA and GLA, PEMULEN is preferably used at a concentration comprised between 0.001% and 2% on the total of the preparation, the preferred concentration being 0.007% by weight.

The proposed compositions may also comprise, as usual, pH adjusters, buffers and sequestering agents such as EDTA, and osmotizing agents, selected from those currently used in the pharmaceutical technology. In the preferred compositions according to the invention an osmotizing agent such as glycerol is used, in an amount suitable to obtain a preparation slightly hypo-osmotic, this feature being useful to counteract the functional and anatomical discomfort of the ocular surface epithelia. Actually, in the cases of hyperevaporation or reduced tear production, an increase in the salt concentration results in an increase of the tear film osmolarity, thus affecting the ocular surface.

Finally, according to some specific embodiments of the invention, the ophthalmic preparations of polyunsaturated fatty acids according to the invention may also contain one or more further antioxidant agents in addition to tocopheryl acetate.

As concerns the preparation process, it is known that the sequence of the various additions of excipients and active ingredients during the preparation of a hydrogel may influence many physical and chemical characteristics of the composition itself, such as viscosity, particles size, degree of dispersion of the active ingredients as well as the system homogeneity. Among the various possible formulative procedures the following one turned out to be the best one:

- dissolution of the gelling polymer (e.g. CARBOPOL);
- addition of the osmotizing agent;
- possible dissolution of the polymeric emulsifier (e.g. PEMULEN);
- addition of the mixture of polyunsaturated fatty acids already mixed with vitamin E, preferably in the form of acetate ester;
- addition of the buffer (e.g. phosphate buffer);
- gelling by addition of NaOH.

All of the additions are to be carried out under mechanical stirring, preferably at 200 rpm.

As pointed out before, the ophthalmic compositions of polyunsaturated fatty acids in solution in vitamin E and dispersed in hydrogel according to the invention turned out to be remarkably more stable to storage than the compositions in emulsion according to the prior art. With reference to a preparation according to the preferred embodiments of the invention, comprising the ethyl ester of EPA and the ethyl ester GLA as active ingredients and α-tocopheryl acetate as antioxidant, CARBOPOL as gelling polymer and glycerol as osmotizing agent, the experimentation showed a surprising stability to storage of the product.

In the same experimental conditions the preparation of EPA and GLA in emulsion have shown a fast degradation kinetics, leading to concentrations of active ingredients of 95% on average already after one month, in spite of the fact that the preparation had been realized under nitrogen and in the presence of antioxidants. It is also surprising that the emulsions of the prior art, in storage conditions at low temperatures (4° C.), are less stable than the hydrogel according to the invention stored at 25° C.

It is believed that the better stability of the omega-3 and omega-6 fatty acids in solution in vitamin E and dispersed in the hydrogel with respect to the stability of the prior art emulsions is due to the fact that the surface of the dispersed oily phase exposed to oxidation is thousands of times greater for the droplets of an emulsion (nanometric size) compared to the surface exposed to oxidation in the product of the present invention. The stirring necessary to form the product, actually, can be adjusted to obtain droplets of about 3 μm average size, and preferably not smaller than 1 μm. Below such figure the degradation phenomena become relevant owing to the high surface that the polyunsaturated fatty acids solution in vitamin E exposes to the interface with the hydrogel. Therefore, the average droplet size of the dispersed phase in the polymeric hydrogel are to be above 1 μm and preferably in the range from 2 to 5 μm.

The compositions proposed according to the invention can be employed as such, in the hydrogel form, or they can be incorporated in a vehicle or carrier consisting of a gel, an ointment, a cream or liposomes, or in any suitable matrix for a topic ophthalmic preparation or an ophthalmic administration, namely with the proviso that such system keeps and does not disrupt the homogeneity of the solution of omega 3 and omega 6 fatty acids in vitamin E acetate.

The specific features of the invention, as well as the advantages of the same, will appear more evident with reference to the detailed description presented by way of example in the following, together with the results of the experimentation carried out on the invention and a comparison with the prior art. Some of the experimental results are also shown in the enclosed drawings, wherein.

Figure 1:
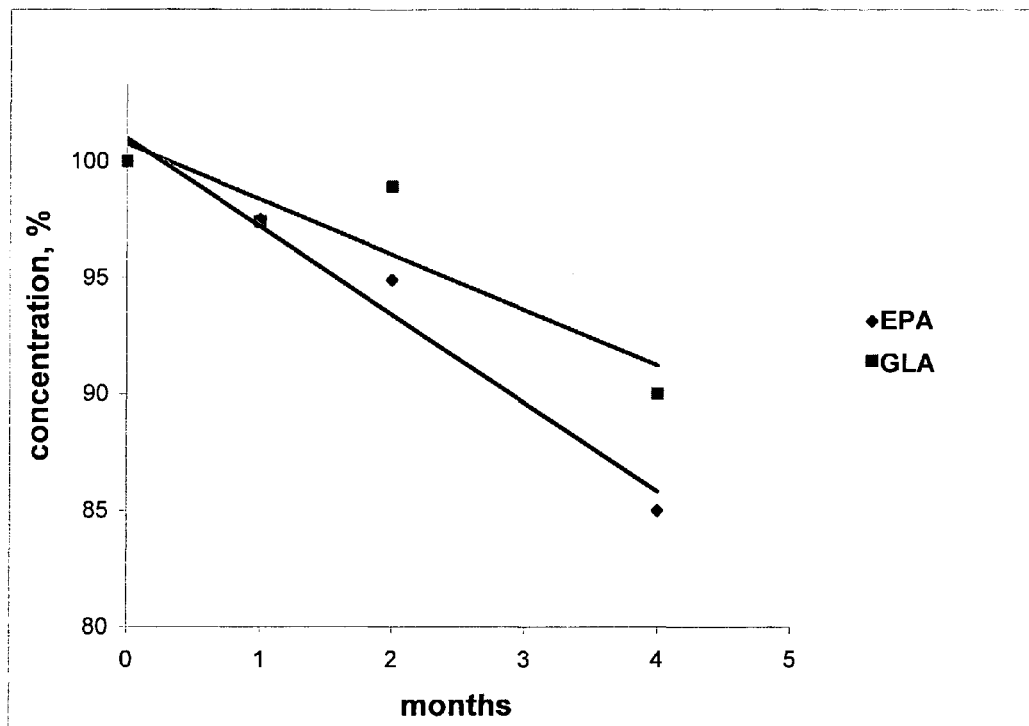
FIG. 1 shows in histogram form the results of a chemical stability study carried out on a preparation of EPA and GLA in phospholipidic emulsion, maintained under refrigerated conditions (4° C.)

Examples where the omega-3 and omega-6 fatty acids, in the form of the respective ethyl esters (EE), are formulated in the hydrogel system according to the present invention are reported below.

EXAMPLE 1

Hydrogel with EPA and GLA

In the formulation according to the invention EPA with a 90% purity and GLA with a 70% purity are employed, both in the form of ethylate. The ingredients employed were as follows:

| Components | % w/w | Function |
| --- | --- | --- |
| EPA EE | 0.40 | active ingredient |
| GLA EE | 0.10 | active ingredient |
| α-tocopheryl acetate | 0.50 | antioxidant |
| CARBOPOL 980 | 0.20 | gelling agent |
| Glycerol | 1.15 | osmotizer |
| NaOH | 0.07 | pH adjuster |
| Disodic Sodium phosphate | 0.10 | pH adjuster |
| Water for injectable preparations | QSP 100 | aqueous phase | pH = 6.90
mOsm = 155

The preparation has been carried out according to the procedure described above.

EXAMPLE 2

Hydrogel with EPA and GLA with addition of PEMULEN

For the preparation the same procedure of the previous example has been followed.

| Components | % w/w | Function |
|---|---|---|
| EPA EE | 0.40 | active ingredient |
| GLA EE | 0.10 | active ingredient |
| α-tocopheryl acetate | 0.30 | antioxidant |
| CARBOPOL 980 | 0.20 | gelling agent |
| Glycerol | 1.15 | osmotizer |
| PEMULEN | 0.007 | polimeric emulsifier |
| NaOH | 0.07 | pH adjuster |
| Disodic Sodium phosphate | 0.10 | pH adjuster |
| Water for injectable preparations | QSP 100 | aqueous phase | pH = 6.96
mOsm = 165

EXAMPLES 3-7

Hydrogel with EPA, DHA and GLA with Addition of PEMULEN

In the preparations of the following examples the omega-3 polyunsaturated fatty acids EPA and DHA, and the omega-6-polyunsaturated acid GLA were employed, all in the form of the corresponding ethyl esters. These turned out to be miscible in all proportions with vitamin E acetate, and were formulated in different ratios in the oily phase.

Subsequently, the fatty acids solutions in vitamin E acetate in various proportions were distributed within a hydrogel of CARBOPOL 980/PEMULEN according to the previously described procedure, ascertaining that the oily solution becomes dispersed in the gel with no phase separation and continues to maintain its integrity of solution, dispersed in droplets of micrometric size in the gel.

The various overall compositions, all at 1% by weight of oily phase in the hydrogel, had pH=7, osmolarity=155 mOsm/kg and average size of the oily droplets of 3 μm.
(table follows)

| | Example No. | | | | |
|---|---|---|---|---|---|
| | 3 | 4 | 5 | 6 | 7 |
| EPA EE | 6.25% | 5% | 20% | 25% | 12.5% |
| DHA EE | 6.25% | 5% | 20% | 25% | 12.5% |
| GLA EE | 12.5% | 40% | 10% | 25% | 50% |
| vit. E acetate | 75% | 50% | 50% | 25% | 25% |
| omega 3/6 ratio | 1:1 | 1:4 | 4:1 | 2:1 | 1:2 |
| Total PUFA | 25% | 50% | 50% | 75% | 75% |
| oily phase (PUFA + vit. E acetate) | 1.00 | 1.00 | 1.00 | 1.00 | 1.00 |
| CARBOPOL 980 (gelling agent) | 0.20 | 0.20 | 0.20 | 0.20 | 0.20 |
| glycerol (osmotizing agent) | 1.15 | 1.15 | 1.15 | 1.15 | 1.15 |
| PEMULEN (polymeric emulsifier) | 0.007 | 0.007 | 0.007 | 0.007 | 0.007 |
| NaOH (pH adjuster) | 0.07 | 0.07 | 0.07 | 0.07 | 0.07 |
| Disodic Sodium phosphate (pH adjuster) | 0.10 | 0.10 | 0.10 | 0.10 | 0.10 |
| purified water | q.s. to 100 | q.s. to 100 | q.s. to 100 | q.s. to 100 | q.s. to 100 |

Physical Characteristics and Stability Studies

An aqueous phase can be dispersed in a gel and stably remain in such condition when the medium viscosity is sufficiently high to block the oil droplets within the same. The studies carried out in the frame of the present invention had shown that the gel is able to "trap" useful amounts of the oily phase consisting of polyunsaturated omega-3/omega-6 fatty acids in solution in α-tocopheryl acetate and to preserve its stability, both physical and chemical.

The formulated gels, described in examples 1-7, upon centrifugation for 15 minutes at the centrifugal force of 11200 g did not evidence any phase separation between dispersed oil and the dispersing hydrogel phase. Also measure of an optical kind, directed to evidence possible phase separations, have confirmed the surprising physical stability of this system.

Chemical Stability

After one month of storage at the temperature of 25° c. EPA and GLA contained in the product of Example 1 have shown a concentration, respectively, of 100% and 101%. Surprisingly, also after three months of storage in the above experimental conditions the concentrations remained substantially unchanged, as reported in the following table.

TABLE 1

Stability of the hydrogel of Example 1 at the temperature of 25° C.

| Detections | | | Osmolarity | | |
|---|---|---|---|---|---|
| Temperature | months | pH 6.2-7.4 | 135-170 mOsm/Kg | % EPA 90.0%-110% | % GLA 90.0%-110% |
| 25° C. | 1 | 6.99 | 150 | 100 | 101 |
| | 2 | 7.01 | 155 | 100 | 101 |
| | 3 | 6.95 | 158 | 99.0 | 99.0 |

COMPARATIVE EXAMPLE 1

In order to ascertain the characteristics of the preparation according to the invention in comparison with preparations in emulsion of the type of those described in connection with the prior art, with particular reference to document EP 0391369, an emulsion containing omega-3 and omega-6 fatty acids has been produced employing MCT (medium chain triglycerides) as the oily and polyoxyethylene sorbitan monooleate (Tween 80) as surface active agent, as reported below.
(table follows)

Example of a EPA-GLA Formulation in Phospholipidic Emulsion

| Components | % w/w | Function |
|---|---|---|
| EPA | 0.4 | active ingredient |
| GLA | 0.1 | active ingredient |
| MCT | 1.5 | oily phase |
| Phospholipon 90 g | 0.375 | emulsifier |
| Tween 80 | 0.5 | surfactant |
| Glycerol | 1.125 | osmotizer |
| α-tocopheryl | 0.2 | antioxidant |
| EDTA-Na$_2$ | 0.1 | chelating agent |
| Water for injectable preparations | QSP 100 | aqueous phase |

The preparation has been realized by following the teachings of the cited patent document.

The emulsion obtained has been studied to evaluate its chemico-physical stability.

The physical stability of the emulsion has been followed by means by light scattering experiments, using a laser source He—Ne (633 nm) at the potency of 10 mW. It results that the particles in emulsion have an average hydrodynamic radius, (r), of 110 nm and a polydispersity of 0.07%. From electrophoretic mobility measures the Z potential has been evaluated, which resulted to be 39±3 mV. This means that the particles endowed with the quite negative surface reject each other, thus avoiding the any coalescence and aggregation phenomenon.

After one month from the preparation such values remain substantially unchanged, thus showing that the emulsion system has a good physical stability, but the experiments carried out in the second month show that the Z potential was become much less negative and that the size of the particles were grown in a significant manner (table 2).

TABLE 2

Stability of the sizes and potential Z of the oily particles in phospholipidic emulsion EPA-GLA

| Time (months) | Dimensions (nm) | Potential Zeta (mV) |
|---|---|---|
| 0 | 110 | −39 |
| 1 | 135 | −40 |
| 2 | 176 | −24 |

All the above shows the evolution of the emulsion towards the phase separation.

For the stability study of the emulsion from the chemical point of view the concentration of EPA and GLA were measured by gas chromatography. As shown in the following Table 3, and as it is also diagrammatically reported in FIG. 1 of the enclosed drawings, the measure of the concentrations after storage of the formulations at a temperature of 4° C. show since the first month a significant reduction of the EPA and GLA concentrations, which are, respectively, 97.5% and 97.4% of the concentration at zero time. The tendency to degradation has been confirmed in the following months, as reported in Table 3 in the corresponding diagram.

TABLE 3

Stability of EPA-GLA in phospholipidic emulsion at 4° C.

| Detections | | pH | Osmolarity 135-170 | % EPA | % GLA |
|---|---|---|---|---|---|
| Temperature | months | 6.2-7.4 | mOsm/Kg | 90.0%-110% | 90.0%-110% |
| 4° C. | 1 | 7.03 | 150 | 97.5 | 97.4 |
| | 2 | 7.02 | 155 | 94.9 | 98.9 |
| | 4 | 6.90 | 150 | 85 | 90 |

In conclusion, the composition studied turned out to be unstable from the physical point of view and, more dramatically, from the chemical point of view.

COMPARATIVE EXAMPLE 2

Since the main degradation products responsible for the reduction of the concentration of EPA and GLA in Comparative Example 1 are oxidation product, the same preparation has been produced in such a way as to limit the oxidability of the product, by bubbling nitrogen during the emulsification step and in the presence of antioxidants.

The phospholipidic emulsion preparation thus obtained has been analyzed for its chemical stability according to the same procedures as the previous example. As it is shown in the following table, after one month of storage at temperature of 25° C. EPA and GLA have shown, respectively, a concentration of 96% and of 95.2% with respect to zero time.

TABLE 4

Stability at 25° C. of EPA-GLA in phospholipidic emulsion prepared under nitrogen

| Detections | | pH | Osmolarity 135-170 | % EPA | % GLA |
|---|---|---|---|---|---|
| Temperature | months | 6.2-7.4 | mOsm/Kg | 90.0%-110% | 90.0%-110% |
| 25° C. | 0 | 7.25 | 145 | 100 | 100 |
| | 1 | 6.86 | 150 | 96.0 | 95.2 |

In spite of the preparation under nitrogen and in presence of further antioxidants, the chemical stability data for this formulation were disappointing. From such data it results the impossibility of storing the eye-drops for a possible commercial use, both in room temperature conditions and under refrigerated conditions.

COMPARATIVE EXAMPLE 3

The direct emulsion of polyunsaturated omega-3 and omega-6 fatty acids with the aid of surfactants according to the disclosure of document WO 2006/007510 has been tested in the laboratories of the Applicant.

In particular, the minimum concentration of surfactant useful to formulate the active ingredients has been determined, and it has been established that values below 1% are not sufficient to obtain emulsion stable from the physical point of view. Formulations with the higher surfactant contents would in any case appear disadvantageous in that the surfactants, as it is known, are very often responsible for toxicity problems to the ocular tissues and are particularly unsuitable in the event of chronic therapies.

From a chemical point of view the preparations have shown oxidation problems similar to those already observed for the preparation described in Comparative Examples 1 and 2. Actually, after one month of storage of composition at a temperature of 25° C., EPA and GLA have shown a concentration of, respectively, 96.5% and 97.0%, thus showing rapid degradation in time of the two "active ingredients" also in this kind of formulation, as it is shown in the following table.

TABLE 5

Stability of EPA and GLA in emulsion according to WO 2006/007510

| Detections | | pH | Osmolarity 135-170 | % EPA | % GLA |
|---|---|---|---|---|---|
| Temperature | months | 6.2-7.4 | mOsm/Kg | 90.0%-110% | 90.0%-110% |
| 25° C. | 0 | 7.25 | 150 | 100 | 100 |
| | 1 | 6.95 | 155 | 96.5 | 97.0 |

For better safety, the examples of compositions described in Table 1 of WO2006/007510, reproduced in Table 6 below, have been repeated, using EPA and DHA as omega-3, both as ethyl esters and as the corresponding triglycerides (EPA EE, DHA EE, EPA TG, DHA TG), and GLA as omega-6, both as ethyl ester and as the corresponding triglyceride (GLA EE, GLA TG).

(table follows)

TABLE 6

Illustrative formulations according to WO 2006/007510

| | Formulation No. | | | | | | | |
|---|---|---|---|---|---|---|---|---|
| | 1 | | 2 | | 3 | | 4 | |
| weight. % ratio omega-3/omega-6 | 0.1/0.1 | | 0.4/01 | | 1.0/1.0 | | 4.0/1.0 | |
| Weight (g)/% | g | % | g | % | g | % | g | % |
| Glucam E-20 | 14.79 | 1.48 | 19.64 | 1.964 | 19.57 | 1.96 | 19.23 | 3.81 |
| Tween 80 | 14.71 | 1.47 | 19.80 | 1.980 | 19.60 | 1.96 | 19.43 | 3.85 |
| buffer sol.[1] | 968.4 | 96.85 | 955.8 | 95.58 | 942 | 94.20 | 442.03 | 87.55 |
| omega 3 | 1.01 | 0.1 | 4.01 | 0.401 | 10.0 | 1.0 | 19.23 | 3.81 |
| omega 6 | 0.99 | 0.099 | 0.99 | 0.099 | 9.97 | 1.0 | 4.95 | 0.98 |
| vitamin E | 1 drop | — | 1 drop | — | 1 drop | — | 1 drop | — |

[1]Buffer solution: NaCl 0.83%; $H_3BO_3$ 0.89%; $Na_2B_4O_7 \times 10\ H_2O$ 0.23%; EDTA 0.01% $H_2O$ 98.04%.

The stability data obtained from each of the four formulations and from each of the three tested fatty acids both in form of ethyl esther and of triglyceride, and both at 4° C. or at 25° C., are shown in the following Tables 7-10.

(table follows)

TABLE 7

Stability of the formulations No. 1 of Table 6

| Detections | | Omega 3 % EPA EE Concentration | Omega 3 % DHA EE Concentration | Omega 6 % GLA EE Concentration |
|---|---|---|---|---|
| Temperature | Months | % | % | % |
| 4° C. | 1 | 96 | 95 | 96 |
| | 2 | 92 | 91 | 91 |
| | 3 | 88 | 86 | 85 |
| | 4 | 82 | 84 | 81 |

| Detections | | Omega 3 % EPA TG Concentration | Omega 3 % DHA TG Concentration | Omega 6 % GLA TG Concentration |
|---|---|---|---|---|
| Temperature | Months | % | % | % |
| 4° C. | 1 | 99 | 99 | 97 |
| | 2 | 97 | 98 | 96 |
| | 3 | 95 | 95 | 94 |
| | 4 | 91 | 91 | 89 |

| Detections | | Omega 3 % EPA EE Concentration | Omega 3 % DHA EE Concentration | Omega 6 % GLA EE Concentration |
|---|---|---|---|---|
| Temperature | Months | % | % | % |
| 25° C. | 1 | 88 | 89 | 90 |
| | 2 | 82 | 80 | 79 |
| | 3 | 65 | 67 | 64 |
| | 4 | 49 | 51 | 47 |

| Detections | | Omega 3 % EPA TG Concentration | Omega 3 % DHA TG Concentration | Omega 6 % GLA TG Concentration |
|---|---|---|---|---|
| Temperature | Months | % | % | % |
| 25° C. | 1 | 90 | 91 | 92 |
| | 2 | 81 | 83 | 82 |
| | 3 | 76 | 77 | 77 |
| | 4 | 67 | 67 | 64 |

TABLE 8

Stability of the formulations No. 2 of Table 6

| Detections | | Omega 3 % EPA EE Concentration | Omega 3 % DHA EE Concentration | Omega 6 % GLA EE Concentration |
|---|---|---|---|---|
| Temperature | Months | % | % | % |
| 4° C. | 1 | 96 | 96 | 98 |
| | 2 | 91 | 90 | 93 |
| | 3 | 87 | 87 | 87 |
| | 4 | 82 | 85 | 81 |

| Detections | | Omega 3 % EPA TG Concentration | Omega 3 % DHA TG Concentration | Omega 6 % GLA TG Concentration |
|---|---|---|---|---|
| Temperature | Months | % | % | % |
| 4° C. | 1 | 98 | 100 | 98 |
| | 2 | 97 | 99 | 96 |
| | 3 | 94 | 97 | 95 |
| | 4 | 92 | 95 | 91 |

| Detections | | Omega 3 % EPA EE Concentration | Omega 3 % DHA EE Concentration | Omega 6 % GLA EE Concentration |
|---|---|---|---|---|
| Temperature | Months | % | % | % |
| 25° C. | 1 | 94 | 95 | 93 |
| | 2 | 85 | 84 | 82 |
| | 3 | 78 | 78 | 75 |
| | 4 | 66 | 68 | 64 |

| Detections | | Omega 3 % EPA TG Concentration | Omega 3 % DHA TG Concentration | Omega 6 % GLA TG Concentration |
|---|---|---|---|---|
| Temperature | Months | % | % | % |
| 25° C. | 1 | 98 | 98 | 100 |
| | 2 | 91 | 90 | 90 |
| | 3 | 82 | 81 | 82 |
| | 4 | 73 | 73 | 70 |

TABLE 9

Stability of the formulations No. 3 of Table 6

| Detections | | Omega 3 % EPA EE Concentration | Omega 3 % DHA EE Concentration | Omega 6 % GLA EE Concentration |
|---|---|---|---|---|
| Temperature | Months | % | % | % |
| 4° C. | 1 | 95 | 96 | 97 |
|  | 2 | 92 | 91 | 91 |
|  | 3 | 88 | 87 | 86 |
|  | 4 | 81 | 84 | 82 |

| Detections | | Omega 3 % EPA TG Concentration | Omega 3 % DHA TG Concentration | Omega 6 % GLA TG Concentration |
|---|---|---|---|---|
| Temperature | Months | % | % | % |
| 4° C. | 1 | 98 | 99 | 98 |
|  | 2 | 97 | 98 | 97 |
|  | 3 | 94 | 95 | 94 |
|  | 4 | 91 | 91 | 89 |

| Detections | | Omega 3 % EPA EE Concentration | Omega 3 % DHA EE Concentration | Omega 6 % GLA EE Concentration |
|---|---|---|---|---|
| Temperature | Months | % | % | % |
| 25° C. | 1 | 94 | 93 | 94 |
|  | 2 | 87 | 87 | 82 |
|  | 3 | 75 | 74 | 74 |
|  | 4 | 68 | 69 | 68 |

| Detections | | Omega 3 % EPA TG Concentration | Omega 3 % DHA TG Concentration | Omega 6 % GLA TG Concentration |
|---|---|---|---|---|
| Temperature | Months | % | % | % |
| 25° C. | 1 | 99 | 98 | 98 |
|  | 2 | 92 | 92 | 91 |
|  | 3 | 82 | 84 | 80 |
|  | 4 | 73 | 75 | 71 |

TABLE 10

Stability of the formulations No. 4 of Table 6

| Detections | | Omega 3 % EPA EE Concentration | Omega 3 % DHA EE Concentration | Omega 6 % GLA EE Concentration |
|---|---|---|---|---|
| Temperature | Months | % | % | % |
| 4° C. | 1 | 94 | 96 | 96 |
|  | 2 | 90 | 95 | 91 |
|  | 3 | 86 | 90 | 86 |
|  | 4 | 81 | 83 | 82 |

| Detections | | Omega 3 % EPA TG Concentration | Omega 3 % DHA TG Concentration | Omega 6 % GLA TG Concentration |
|---|---|---|---|---|
| Temperature | Months | % | % | % |
| 4° C. | 1 | 98 | 100 | 97 |
|  | 2 | 96 | 98 | 95 |
|  | 3 | 94 | 96 | 93 |
|  | 4 | 92 | 93 | 89 |

TABLE 10-continued

Stability of the formulations No. 4 of Table 6

| Detections | | Omega 3 % EPA EE Concentration | Omega 3 % DHA EE Concentration | Omega 6 % GLA EE Concentration |
|---|---|---|---|---|
| Temperature | Months | % | % | % |
| 25° C. | 1 | 95 | 93 | 92 |
|  | 2 | 89 | 88 | 81 |
|  | 3 | 75 | 77 | 74 |
|  | 4 | 67 | 70 | 68 |

| Detections | | Omega 3 % EPA TG Concentration | Omega 3 % DHA TG Concentration | Omega 6 % GLA TG Concentration |
|---|---|---|---|---|
| Temperature | Months | % | % | % |
| 25° C. | 1 | 97 | 98 | 99 |
|  | 2 | 90 | 92 | 92 |
|  | 3 | 83 | 83 | 84 |
|  | 4 | 75 | 74 | 73 |

The foregoing data further confirm that polyunsaturated fatty acids omega- and omega-6, formulated in emulsion for topical use, are rapidly degraded, both they are included in the formulation as ethyl esters and when the corresponding triglycerides are used. Such instability is common to other emulsive systems of the prior art, and confirms in general what reported in the literature concerning the chemical stability of the polyunsaturated fatty acids.

Stability Studies on the Compositions of Examples 3-7

In order to perform an accurate comparison between the stability of the prior art compositions and the stability of the ophthalmic preparation according to the invention, the chemical stability of the oily phases of the compositions described in Examples 3-7 has first been evaluated. The corresponding data are reported in the following table.

TABLE 11

Stability of the oily phases of Examples 3-7 according to the invention
Concentration of PUFA determined after 12 months at 25° C.

| | Example No. | | | | |
|---|---|---|---|---|---|
| | 3 | 4 | 5 | 6 | 7 |
| EPA EE | 6.25% | 5% | 20% | 25% | 12.5 |
| DHA EE | 6.25% | 5% | 20% | 25% | 12.5 |
| GLA EE | 12.5% | 40% | 10% | 25% | 50 |
| vit. E acetate | 75% | 50% | 50% | 25% | 25% |
| omega 3/6 ratio | 1:1 | 1:4 | 4:1 | 2:1 | 1:2 |
| Total PUFA | 25% | 50% | 50% | 75% | 75% |
| EPA concn % | 100 | 100 | 99 | 97 | 96 |
| DHA concn % | 99 | 99 | 100 | 96 | 96 |
| GLA concn % | 100 | 99 | 100 | 97 | 97 |

The foregoing shows that compositions having total concentration of polyunsaturated fatty acids up to 50% in α-tocopheryl acetate exhibit a surprising stability. Only at fatty acids concentrations above 50%, when vitamin E acetate is reduced below 50%, a slight degradation starts to become apparent. In addition, the omega-e and omega-6 fatty acids both as triglycerides and as phospholipids (in particular, krill oil) have shown even better stabilities. Therefore the preceding table shows the "worst" case of stability which is the case of ethyl esters of omega-3 and 6.

The formulations of polyunsaturated fatty acids in vitamin E acetate, although extremely stable, would be poorly useful for ophthalmic formulations owing to their low tolerability, but they can be stored as such for long periods of time, also beyond the same stability of the pure PUFAs.

Starting from the oily mixtures described it is sufficient to add CARBOPOL 980 and PEMULEN, and accordingly produce the polymeric hydrogel to obtain a perfect tolerability and maintain the composition stability. The results of the stability test in the complete formulation of Examples 3-6 (table, Examples 3-7, page 19) are reported below.

(table follows)

TABLE 12

Stability of the formulation of Example 3 according to the invention
Concentration in hydrogel 1% - Average size of oily droplets 3 μm

| Detections | | Omega 3 % EPA EE Concentration | Omega 3 % DHA EE Concentration | Omega 6 % GLA EE Concentration |
|---|---|---|---|---|
| Temperature | Months | % | % | % |
| 4° C. | 3 | 100 | 100 | 101 |
|  | 6 | 101 | 99 | 101 |
|  | 9 | 99 | 100 | 100 |
|  | 12 | 100 | 99 | 98 |

| Detections | | Omega 3 % EPA TG Concentration | Omega 3 % DHA TG Concentration | Omega 6 % GLA TG Concentration |
|---|---|---|---|---|
| Temperature | Months | % | % | % |
| 4° C. | 3 | 100 | 99 | 100 |
|  | 6 | 102 | 100 | 101 |
|  | 9 | 100 | 99 | 100 |
|  | 12 | 100 | 99 | 98 |

| Detections | | Omega 3 % EPA EE Concentration | Omega 3 % DHA EE Concentration | Omega 6 % GLA EE Concentration |
|---|---|---|---|---|
| Temperature | Months | % | % | % |
| 25° C. | 3 | 100 | 100 | 99 |
|  | 6 | 100 | 99 | 99 |
|  | 9 | 97 | 98 | 97 |
|  | 12 | 95 | 95 | 96 |

| Detections | | Omega 3 % EPA TG Concentration | Omega 3 % DHA TG Concentration | Omega 6 % GLA TG Concentration |
|---|---|---|---|---|
| Temperature | Months | % | % | % |
| 25° C. | 3 | 101 | 99 | 100 |
|  | 6 | 99 | 100 | 100 |
|  | 9 | 100 | 97 | 98 |
|  | 12 | 97 | 97 | 98 |

TABLE 13

Stability of the formulation of Example 4 according to the invention
Concentration in hydrogel 1% - Average size of oily droplets 3 μm

| Detections | | Omega 3 % EPA EE Concentration | Omega 3 % DHA EE Concentration | Omega 6 % GLA EE Concentration |
|---|---|---|---|---|
| Temperature | Months | % | % | % |
| 4° C. | 3 | 101 | 100 | 100 |
|  | 6 | 100 | 101 | 99 |
|  | 9 | 98 | 97 | 99 |
|  | 12 | 98 | 100 | 99 |

TABLE 13-continued

Stability of the formulation of Example 4 according to the invention
Concentration in hydrogel 1% - Average size of oily droplets 3 μm

| Detections | | Omega 3 % EPA TG Concentration | Omega 3 % DHA TG Concentration | Omega 6 % GLA TG Concentration |
|---|---|---|---|---|
| Temperature | Months | % | % | % |
| 4° C. | 3 | 100 | 99 | 101 |
|  | 6 | 98 | 100 | 99 |
|  | 9 | 99 | 100 | 99 |
|  | 12 | 100 | 98 | 100 |

| Detections | | Omega 3 % EPA EE Concentration | Omega 3 % DHA EE Concentration | Omega 6 % GLA EE Concentration |
|---|---|---|---|---|
| Temperature | Months | % | % | % |
| 25° C. | 3 | 99 | 99 | 100 |
|  | 6 | 100 | 100 | 99 |
|  | 9 | 98 | 97 | 95 |
|  | 12 | 95 | 96 | 94 |

| Detections | | Omega 3 % EPA TG Concentration | Omega 3 % DHA TG Concentration | Omega 6 % GLA TG Concentration |
|---|---|---|---|---|
| Temperature | Months | % | % | % |
| 25° C. | 3 | 100 | 99 | 100 |
|  | 6 | 99 | 100 | 101 |
|  | 9 | 99 | 96 | 98 |
|  | 12 | 96 | 97 | 97 |

TABLE 14

Stability of the formulation of Example 5 according to the invention
Concentration in hydrogel 1% - Average size of oily droplets 3 μm

| Detections | | Omega 3 % EPA EE Concentration | Omega 3 % DHA EE Concentration | Omega 6 % GLA EE Concentration |
|---|---|---|---|---|
| Temperature | Months | % | % | % |
| 4° C. | 3 | 101 | 99 | 100 |
|  | 6 | 99 | 100 | 101 |
|  | 9 | 100 | 98 | 99 |
|  | 12 | 98 | 99 | 99 |

| Detections | | Omega 3 % EPA TG Concentration | Omega 3 % DHA TG Concentration | Omega 6 % GLA TG Concentration |
|---|---|---|---|---|
| Temperature | Months | % | % | % |
| 4° C. | 3 | 100 | 98 | 99 |
|  | 6 | 101 | 101 | 100 |
|  | 9 | 100 | 99 | 98 |
|  | 12 | 101 | 100 | 99 |

| Detections | | Omega 3 % EPA EE Concentration | Omega 3 % DHA EE Concentration | Omega 6 % GLA EE Concentration |
|---|---|---|---|---|
| Temperature | Months | % | % | % |
| 25° C. | 3 | 98 | 99 | 100 |
|  | 6 | 97 | 98 | 99 |
|  | 9 | 95 | 97 | 97 |
|  | 12 | 95 | 95 | 94 |

TABLE 14-continued

Stability of the formulation of Example 5 according to the invention
Concentration in hydrogel 1% - Average size of oily droplets 3 μm

| Detections | | Omega 3 % EPA TG Concentration | Omega 3 % DHA TG Concentration | Omega 6 % GLA TG Concentration |
|---|---|---|---|---|
| Temperature | Months | % | % | % |
| 25° C. | 3 | 99 | 98 | 99 |
| | 6 | 98 | 100 | 100 |
| | 9 | 100 | 98 | 97 |
| | 12 | 96 | 97 | 96 |

TABLE 15

Stability of the formulation of Example 6 according to the invention
Concentration in hydrogel 1% - Average size of oily droplets 3 μm

| Detections | | Omega 3 % EPA EE Concentration | Omega 3 % DHA EE Concentration | Omega 6 % GLA EE Concentration |
|---|---|---|---|---|
| Temperature | Months | % | % | % |
| 4° C. | 3 | 101 | 100 | 100 |
| | 6 | 100 | 101 | 99 |
| | 9 | 98 | 97 | 98 |
| | 12 | 98 | 98 | 98 |

| Detections | | Omega 3 % EPA TG Concentration | Omega 3 % DHA TG Concentration | Omega 6 % GLA TG Concentration |
|---|---|---|---|---|
| Temperature | Months | % | % | % |
| 4° C. | 3 | 100 | 99 | 101 |
| | 6 | 98 | 100 | 99 |
| | 9 | 99 | 99 | 98 |
| | 12 | 98 | 98 | 99 |

| Detections | | Omega 3 % EPA EE Concentration | Omega 3 % DHA EE Concentration | Omega 6 % GLA EE Concentration |
|---|---|---|---|---|
| Temperature | Months | % | % | % |
| 25° C. | 3 | 99 | 99 | 101 |
| | 6 | 99 | 98 | 98 |
| | 9 | 97 | 96 | 95 |
| | 12 | 93 | 92 | 93 |

| Detections | | Omega 3 % EPA TG Concentration | Omega 3 % DHA TG Concentration | Omega 6 % GLA TG Concentration |
|---|---|---|---|---|
| Temperature | Months | % | % | % |
| 25° C. | 3 | 100 | 99 | 101 |
| | 6 | 98 | 98 | 98 |
| | 9 | 97 | 96 | 97 |
| | 12 | 94 | 95 | 94 |

Tolerability and Activity Tests

Ocular Acute Tolerability of the Eye-Drops According to the Invention

The ocular tolerability of the eye-drops in hydrogel of the Example 1 (MDV0705 IDROGEL) has been evaluated after three instillations at 2 hours one after another in rabbits' eyes. Two drops of product were instilled in the right eye of each animal for a total of 3 times a day at 2 hour time intervals. The group of rabbits consisted of 8 animals (4 males, 4 females).

The conditions of the ocular tissues were observed in accordance with the Draize test.

The examination was carried out after the third instillation on the day of treatment, and again 24, 48 and 72 hours after the first instillation, assigning arbitrary scores to the various aspects of the conjunctiva, of the iris and of the cornea.

No significant reddening has been observed in the conjunctive for the whole period of the test, both in the eyes treated with the MDV0705 IDROGEL and in the eyes treated with placebo.

No edema or opacity at corneal level has been observed. In addition, no implications on the iris were noted.

The presence of drainage material remained at a normal level.

The results obtained show that the ophthalmic preparation in hydrogel according to the invention was well tolerated after repeated installation (three in 6 hours), and the no difference with respect to placebo is evidenced.

Clinical Tolerability Tests

The instillation of the MDV0705 IDROGEL eye-drops on a group of 20 normal subjects, without any sign of sufferance on the ocular surface and with a normal tear secretion, did not produce any significant undesired effect.

In particular, the subjects who received the eye-drops under test were given a questionnaire of 2 questions, to which the subjects had to reply after 1, 5, 10 and 60 minutes. To question 1 ("Did you feel any pain after instillation of the eye-drops?"), 100% of the subjects answered "no" at each control; to question 2 ("Did you feel any nuisance after the instillation of the eye-drops?"), 100% of the subjects answered "no" at each control.

Evaluation of the Activity of the Preparation in Hydrogel According to the Invention in the Treatment of Dry Eye Syndrome.

Considering that preparation MDV0705 IDROGEL containing omega-3 and omega-6 fatty acids appeared to be endowed with characteristics of protection of the ocular surface and of reduction of inflammation, once ascertained its tolerability, its activity on the treatment of patient suffering from dry eye syndrome has been ascertained. The product has been compared with a commercial tear substitute consisting of a lipid emulsion, i.e. the Lipimix eye-drops (Tubilux, Italia), the only tear substitute containing lipids presently on the market.

The activity of MDV0705 IDROGEL has been evaluated in a group of patients (n=5) with dry eye syndrome and has a control (n=5) patients with dry-eye syndrome treated with Lipimix have been employed. The patients instilled MDV0705 IDROGEL and Lipimix 3 times a day in both eyes and the controls were performed after 7 days of treatment. The right eye has been used for the statistical analysis of the results.

The patients with dry-eye syndrome had been selected following the inclusion criteria recognized internationally (The definition and classification of dry eye disease. Subcommittee of the International Dry Eye Workshop, *Ocul. Surf.* 2007; 5:75-92) and more precisely:

Symptoms of ocular dryness, detected by using a proper questionnaire, with a codified system for score assigning (Shiffman R M, Dale Christianson M, Jacobsen G, Hirsch J D, Reis B L. Reliability and validity of the Ocular Surface Disease Index (OSDI), *Arch. Ophthalmol.* 2000; 118:615-21);

Fluorescein staining of the cornea, measured according to NEI/Industry workshop Scale>3 (Lemp Mass., Report of the National Eye Institute/Industry workshop on clinical trials in dry eyes. *CLAO J.* 1995; 21:221-232);

Break-up time (BUT)<10 seconds;

Schirmer I test<8 mm at 5 minutes.

Exclusion criteria: infective keratoconjunctivites, positive anamnesis for ocular allergies, ophthalmic or eye-lids surgery in the 3 months preceding the study, nose-lacrimal pathologies, use of steroid-based eye-drops in the 4 weeks preceding the study, diabetes, anti-glaucoma eye-drops.

The parameters used to evaluate the activity of MDV 0705 IDROGEL in comparison with the control have been the following:

Symptoms of ocular dryness (detected with the proper questionnaire)
Tear film beak-up time (BUT)
Schirmer I test Procedures to Evaluate the Break-Up-Time (BUT)

BUT is considered to be an indicator of the tear film stability. The test consists of observing with the slit lamp with a blue cobalt filter the film surface after instillation of fluorescein. During the test the patient keeps his/her eyes open without blinking and looking straight in front of him/her, and the time lapsing from the last blinking and the formation of small dry areas (which appear darker) on the corneal surface is measured, then calculating the average of three subsequent detections.

Schirmer I Test

The Schirmer I test provides information on the lacrimal secretion. It carried out in faintly lit room, placing a paper strip in the lower conjuctival fornix, at the external side and measuring the soaking thereof after 5 minutes. The test has to be performed with standardized procedures, as many variable exist which take part in determining the value. The most important variable derives from the fact that absorption by the absorbent paper strip and the length of the wet portion are influenced by the capillarity force and the wettability of its cellulose fibers. This results in the importance of performing the test with validated paper strips.

Figure 2:
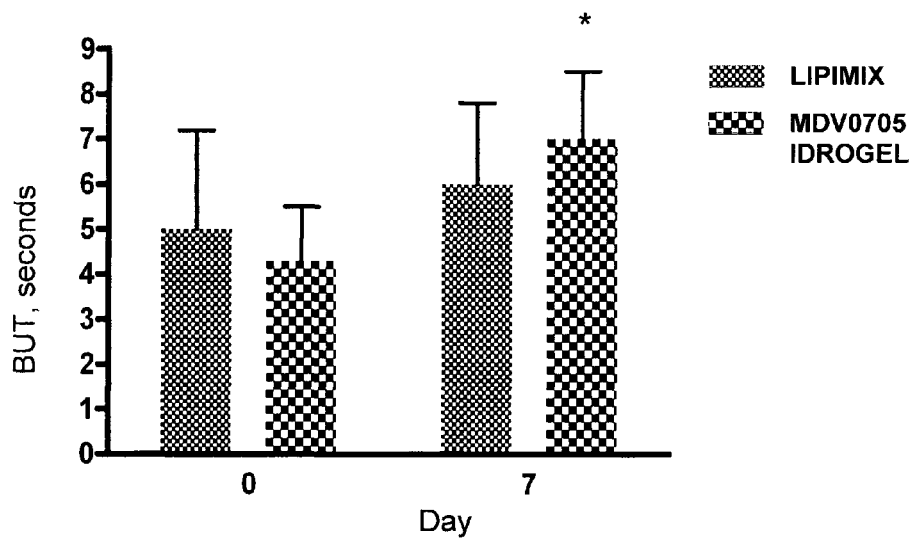
FIG. 2 shows the break-up time (BUT) on day 0 and on day 7 in patients treated with a hydrogel preparation according to the invention, in comparison with a commercial tear substitute in phospholipidic emulsion, i.e. Lipimix (Tubilux, Italy)
Figure 3:
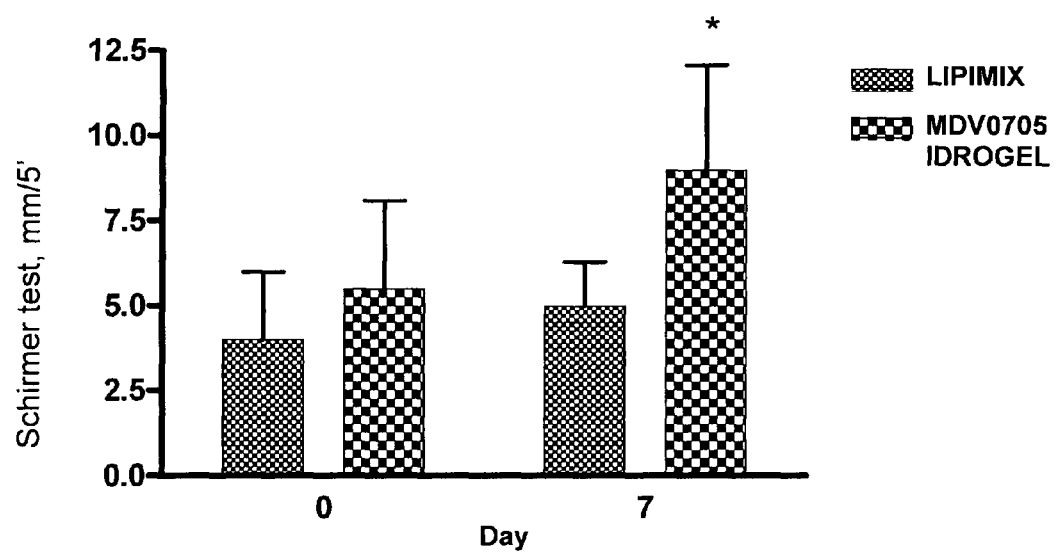
FIG. 3 shows the lacrimal secretion measured with the Schirmer I test on day 0 and on day 7 in patients treated with the preparation in hydrogel according to the invention in comparison with the same commercial product (tear substitute in phospholipidic emulsion) of FIG. 2.

The results of the observational study as concerns the BUT and the Schirmer test are shown, respectively, in FIGS. 2 and 3 of the enclosed drawings. The results on day 7 evidenced a significant improvement in the symptoms and signs of the ocular surface in patients with dry eye syndrome treated with MDV0705 IDROGEL, with respect to the baseline values (day 0). In addition at day 7 the patients treated with MDV0705 IDROGEL had shown a significant improvement ($p<0.05$) of the symptoms with respect to the control group.

The tear film break-up time (BUT) (FIG. 2) on day 7 showed a significant increase with respect to the baseline conditions (day 0) only in the group of patients treated with MDV 0705 IDROGEL.

The lacrimal secretion (FIG. 3) measured with the Schirmer I test showed a significant increase with respect to the starting conditions only in the group of patients treated with MDV0705 IDROGEL, while the group of patients treated with Lipimix showed a non-significant increase of the lacrimal production at 7 days. The comparison on day 7 between patients treated with MDV0705 IDROGEL and Lipimix showed a significant increase of the first group with respect to the second one.

In conclusion, it is confirmed that the possibility of using omega-3 and omega-6 fatty acids in eye-drops represents an important innovation for the treatment of patients suffering from dry eye syndrome, both in reducing the symptoms reported by the patients, and in improving the stability of the tear film, and consequently the conditions of the ocular surface. Such advantageous therapeutic instrument is easily available from the pharmaceutical point of view thank to the improved shelf-life obtainable with the compositions in hydrogel according to the invention.

The present invention has been disclosed with particular reference to some specific embodiments thereof, but it should be understood that modifications and changes may be made by the persons skilled in the art without departing from the scope of the invention as defined in the appended claims.

The invention claimed is:

1. A topical ophthalmic composition containing, as active ingredients, one or more omega-3 polyunsaturated fatty acids and one or more omega-6 polyunsaturated fatty acids, the said fatty acids having an aliphatic chain of from 16 to 24 carbon atoms, or pharmaceutically acceptable derivatives thereof, selected from their esters with $C_1$-$C_6$ alkyl groups, their triglycerides and their phospholipids, in solution with α-tocopheryl acetate, said solution being dispersed in a hydrogel that comprises an aqueous vehicle containing one or more gelling polymers comprising cross-linked carboxyvinyl polymers.

2. The ophthalmic composition according to claim 1, wherein the weight ratio of α-tocopheryl acetate to the source of omega-3 and omega-6 polyunsaturated fatty acids ranges from 4:1 to 1:4.

3. The ophthalmic composition according to claim 1, wherein said omega-3 and omega-6 fatty acids have an aliphatic chain of from 18 to 22 carbon atoms.

4. The ophthalmic composition according to claim 3, containing, as omega-3 polyunsaturated fatty acid, eicosapentaenoic acid (EPA) or a linear or branched $C_1$-$C_6$ alkyl ester thereof, the triglyceride or a phospholipid thereof, docosahexaenoic acid (DHA) or a linear or branched $C_1$-$C_6$ alkyl ester thereof, the triglyceride or a phospholipid thereof, or mixtures of the same.

5. The ophthalmic composition according to claim 3, containing, as omega-6 polyunsaturated fatty acid, γ-linolenic acid (GLA) or a linear or branched $C_1$-$C_6$ alkyl ester thereof, the triglyceride or a phospholipid thereof.

6. The ophthalmic composition according to claim 4, containing as active ingredients EPA, DHA and GLA or their ethyl esters, or their triglycerides or their phospholipids.

7. The ophthalmic composition according to claim 1, containing as active ingredients one or more omega-3 polyunsaturated fatty acids and one or more omega-6 polyunsaturated fatty acids both as triglycerides.

8. The ophthalmic composition according to claim 1, containing as active ingredients one or more omega-3 polyunsaturated fatty acids and one or more omega-6 polyunsaturated fatty acids both as phospholipids.

9. The ophthalmic composition according to claim 1, wherein the weight ratio of omega-3 to omega-6 ranges from 20:1 to 1:20.

10. The ophthalmic composition according to claim 9, wherein the weight ratio of omega-3 to omega-6 ranges from 4:1 to 1:4.

11. The ophthalmic composition according to claim 1, comprising the following ingredients in weight/weight % (Formulation 1):
 0.40% EPA ethyl ester;
 0.10% GLA ethyl ester;
 0.50% α-tocopheryl acetate; and
 0.20% gelling polymer;
wherein the ethyl esters are in the form of ethylate.

12. The ophthalmic composition according to claim 1, also comprising one or more osmolarity adjusting agents.

13. The ophthalmic composition according to claim 1, also comprising one or more polymeric emulsifying agents.

14. The ophthalmic composition according to claim 13, wherein said polymeric emulsifying agents are selected from poloxamers and acrylic acid polymers.

15. The ophthalmic composition according to claim 13, wherein said polymeric emulsifying agent comprises an acrylic acid polymer.

16. The ophthalmic composition according to claim 15, wherein 1% by weight of each of the following formulations is dispersed in a hydrogel comprising:
   0.20% gelling polymer;
   0.007% Acrylate/C10-C30/Alkylacrylate (PEMULEN); and
   water;
and said formulations are selected from the following group of formulations:
   Formulation 3 comprising in weight/weight %:
      6.25% EPA ethyl ester;
      6.25% DHA ethyl ester;
      12.5% GLA ethyl ester; and
      75% Vitamin E acetate;
   Formulation 4 comprising in weight/weight %:
      5% EPA ethyl ester;
      5% DHA ethyl ester;
      40% GLA ethyl ester; and
      50% Vitamin E acetate;
   Formulation 5 comprising in weight/weight %:
      20% EPA ethyl ester;
      20% DHA ethyl ester;
      10% GLA ethyl ester; and
      50% Vitamin E acetate;
   Formulation 6 comprising in weight/weight %:
      25% EPA ethyl ester;
      25% DHA ethyl ester;
      25% GLA ethyl ester; and
      25% Vitamin E acetate; or
   Formulation 7 comprising in weight/weight %:
      12.5% EPA ethyl ester;
      12.5% DHA ethyl ester;
      50% GLA ethyl ester; and
      25% Vitamin E acetate.

17. The ophthalmic composition according to claim 1, comprising EPA ethyl ether, DHA ethyl ether and GLA ethyl ether as active ingredients in solution in α-tocopheryl acetate, carboxyvinyl polymers as gelling polymer and acrylic acid polymers as polymeric emulsifying agent.

18. The ophthalmic composition according to claim 1, wherein said omega-3 and omega-6 polyunsaturated fatty acids are contained in one or more vegetable and/or fish oils, mixed in turn with said α-tocopheryl acetate the resulting mixture being in dispersed form in the said hydrogel.

19. The ophthalmic composition according to claim 18, wherein said vegetable oils are selected from linseed oil, borage oil, wheat germ oil, hempseed oil, olive oil, peanut oil, blackcurrant oil and soybean oil and mixtures thereof, and the said fish oils are selected from salmon oil, mackerel oil, oily fish oil, krill oil and mixtures thereof.

20. A method of preventing or treating ocular pathologies comprising administering to a patient in need thereof a topical ophthalmic composition according to claim 1, wherein the ocular pathology is selected from inflammatory keratitis and conjunctivitis and dry eye syndrome.

21. The ophthalmic composition according to claim 1, wherein the amount of said α-tocopheryl acetate in said solution with the omega-3 and omega-6 polyunsaturated fatty acids is not less than 50% by weight.

22. The ophthalmic composition according to claim 1, wherein the said solution of one or more omega-3 polyunsaturated fatty acids and one or more omega-6 polyunsaturated fatty acids in solution with α-tocopheryl acetate ester thereof, forms a micrometric dispersion dispersed in said hydrogel.

23. The ophthalmic composition according to claim 21, wherein the amount of α-tocopheryl acetate in said solution with the omega 3 and omega 6 polyunsaturated fatty acids the oily mixture of omega 3 and omega 6 is between 50% and 75% by weight.

* * * * *